US012631635B2

(12) United States Patent
Shah et al.

(10) Patent No.: US 12,631,635 B2
(45) Date of Patent: May 19, 2026

(54) SPECIES-SPECIFIC ANTIGEN SEQUENCES FOR TICK-BORNE RELAPSING FEVER (TBRF) AND METHODS OF USE

(71) Applicant: ID-Fish Technology, Inc., Milipitas, CA (US)

(72) Inventors: Jyotsna S. Shah, Santa Clara, CA (US); Song Liu, San Jose, CA (US)

(73) Assignee: ID-Fish Technology, Inc., Milipitas, CA (US)

( * ) Notice: Subject to any disclaimer, the term of this patent is extended or adjusted under 35 U.S.C. 154(b) by 954 days.

(21) Appl. No.: 17/248,236

(22) Filed: Jan. 15, 2021

(65) Prior Publication Data

US 2022/0229055 A1     Jul. 21, 2022

(51) Int. Cl.
*G01N 33/569*     (2006.01)
*C07K 14/20*     (2006.01)

(52) U.S. Cl.
CPC ........ *G01N 33/56911* (2013.01); *C07K 14/20* (2013.01); *C07K 2319/40* (2013.01); *G01N 2333/20* (2013.01); *G01N 2469/20* (2013.01)

(58) Field of Classification Search
CPC ......... G01N 33/56911; G01N 2333/20; G01N 2469/20; C07K 14/20; C07K 2319/20; C07K 2319/40
USPC ............ 424/186.1; 435/7.8, 4; 530/350, 300
See application file for complete search history.

(56) References Cited

U.S. PATENT DOCUMENTS 5,571,718 A * 11/1996 Dunn ..................... C07K 14/20
                                                      536/23.7

2019/0277847 A1     9/2019 Shah et al.
2020/0255889 A1     8/2020 Tokarz et al.

OTHER PUBLICATIONS

Burman N, Bergström S, Restrepo BI, Barbour AG. The variable antigens Vmp7 and Vmp21 of the relapsing fever bacterium Borrelia hermsii are structurally analogous to the VSG proteins of the African trypanosome. Mol Microbiol. Oct. 1990;4(10):1715-26. (Year: 1990).*
Porcella SF, Raffel SJ, Schrumpf ME, Schriefer ME, Dennis DT, Schwan TG. Serodiagnosis of Louse-Borne relapsing fever with glycerophosphodiester phosphodiesterase (GlpQ) from Borrelia recurrentis. J Clin Microbiol. Oct. 2000;38(10):3561-71. (Year: 2000).*
Dai et al. Antigenic variation by Borrelia hermsii occurs through recombination between extragenic repetitive elements on linear plasmids. Mol Microbiol. Jun. 2006;60(6):1329-43. (Year: 2006).*
Lopez JE, Schrumpf ME, Nagarajan V, Raffel SJ, McCoy BN, Schwan TG. A novel surface antigen of relapsing fever spirochetes can discriminate between relapsing fever and Lyme borreliosis. Clin Vaccine Immunol. Apr. 2010;17(4):564-71. (Year: 2010).*
Kingry LC, Batra D, Replogle A, Sexton C, Rowe L, Stermole BM, Christensen AM, Schriefer ME. Chromosome and Linear Plasmid Sequences of a 2015 Human Isolate of the Tick-Borne Relapsing Fever Spirochete, Borrelia turicatae. Genome Announc. Jul. 14, 2016;4(4):e00655-16. (Year: 2016).*

(Continued)

*Primary Examiner* — Christopher L Chin
*Assistant Examiner* — Ellis Follett Lusi
(74) *Attorney, Agent, or Firm* — Pierce Atwood LLP; Christopher A. Baxter

(57)     ABSTRACT

The disclosure, in some aspects, provides antigen-specific amino acid sequences for tick-borne relapsing fever *Borrelia* species.

9 Claims, 3 Drawing Sheets

Specification includes a Sequence Listing.

(56)                    References Cited

OTHER PUBLICATIONS

Schott M, Grosskinsky S, Brenner C, Kraiczy P, Wallich R. Molecular characterization of the interaction of Borrelia parkeri and Borrelia turicatae with human complement regulators. Infect Immun. May 2010;78(5):2199-208. (Year: 2010).*

Schwan TG, Raffel SJ, Schrumpf ME, Policastro PF, Rawlings JA, Lane RS, Breitschwerdt EB, Porcella SF. Phylogenetic analysis of the spirochetes Borrelia parkeri and Borrelia turicatae and the potential for tick-borne relapsing fever in Florida. J Clin Microbiol. Aug. 2005;43(8):3851-9. (Year: 2005).*

Harlow, E. and Lane, D., Antibodies: A Laboratory Manual (1988) Cold Spring Harbor Laboratory Press, Cold Spring Harbor, NY, pp. 23-26. (Year: 1988).*

Lederman et al. A single amino acid substitution in a common African allele of the CD4 molecule ablates binding of the monoclonal antibody, OKT4. Mol Immunol. Nov. 1991;28(11):1171-81) (Year: 1991).*

Colman et al. Research in Immunology, 1994; 145(1): 33-36. (Year: 1994).*

Goel et al. Plasticity within the Antigen Combining Site May Manifest as Molecular Mimicry in the Humoral Immune Response. The Journal of Immunology (2004), 173(12):7358-7367 (Year: 2004).*

Lloyd et al. Modelling the human immune response: performance of a 1011 human antibody repertoire against a broad panel of therapeutically relevant antigens, Protein Engineering, Design & Selection (2009), 22(3):159-168 (Year: 2009).*

Edwards et al. The remarkable flexibility of the human antibody repertoire; isolation of over one thousand different antibodies to a single protein, BlyS, Journal of Molecular Biology (2003), 334:103-118. (Year: 2003).*

Porcella et al. "The genome sequence of Borrelia hermsii and Borrelia turicatae: comparative analysis of two agents of endemic N. America relapsing fever". UniProt ID: A1QyU6_BORT9. UniProt. Apr. 14, 2009. (Year: 2009).*

Lopez et al (Sequence analysis and serological responses against Borrelia turicatae BipA, a putative species-specific antigen. PLoS Negl Trop Dis. Sep. 19, 2013;7(9):e2454) (Year: 2013).*

Sticker, et al. "Chronic Lyme Disease: A Working Case Definition" American Journal of Infectious Disease; 2018; vol. 14(1); 44 pages.

Cameron, et al. "Evidence assessments and guideline recommendations in Lyme disease: the clinical management of known tick bites, erythema migrans rashes and persistent disease" 2014; Expert Rev. Anti Infect. Therapy; vol. 12 (9); 33 pages.

Liu, et al. "Pilot Study of Immunoblots with Recombinant Borrelia burgdorferi Antigens for Laboratory Diagnosis of Lyme Disease" 2018; Healthcare; vol. 6(99); 15 pages.

Shah, et al. "Line Immunoblots Assay for Tick-Borne Relapsing Fever and Findings in Patient Sera From Australia, Ukraine and the USA" 2019; Healthcare; vol. 7(12); 17 pages.

Fesler, et al. "Lyme Disease: Diversity of Borrelia Species in California and Mexico Detected Using a Novel Immunoblot Assay" 2020; Healthcare; vol. 8(97); 16 pages.

International Preliminary Report on Patentability from the International Preliminary Examining Authority dated Feb. 12, 2024 from corresponding International Patent Application No. PCT/US2022/012229 filed on Jan. 13, 2022.

Barbour, AG et al: "In Vitro and In Vivo Neutralization of the Relapsing Fever Agent Borrelia hermsii with Serotype-Specific Immunoglobulin M Antibodies", Infection and Immunity, vol. 69, No. 2, Feb. 1, 2001 (Feb. 1, 2001), pp. 1009-1015, XP055187970, ISSN: 0019-9567, DOI: 10.1128/IAI.69.2.1009-1015.2001.

Partial European Supplementary Search Report dated Dec. 17, 2024 from corresponding European Patent Application No. 22740028.0.

* cited by examiner

Fig. 3

TBRF IgM and IgG Blots - Performance on Patient Serum Samples

TBRF ImmunoBlot IgM

| Antigens | Bip A (70-75kDa) | | | GlpQ | | | BpcA/fHbp | | P41/FlaB | | Vlp7 | Result |
|---|---|---|---|---|---|---|---|---|---|---|---|---|
| SEQ ID NO | 2 | 5 | 6 | 11 | 7 | 10 | 3 | 8 | 4 | 9 | 1 | |
| Sample # | Tt-2 | Pk-1 | Pk-2 | Mia | Pk | Du | Tt | Pk | Tt | Pk | Bh | |
| 1 | | | | | | | | | | | | Neg |
| 2 | Pos | Pos | Pos | | | Pos | | | | | | Pos |
| 3 | | | | - | | | | | | | | Neg |
| 4 | | | | | | | | | | | Pos | Neg |
| 5 | Pos | Pos | Pos | Pos | Pos | | Pos | | Pos | - | Pos | Pos |
| 6 | | | | | | - | | | | | | Neg |
| 7 | | | | | | Pos | | Pos | | Pos | | Pos |
| 8 | | | | | | | | | | | | Neg |
| 9 | | | | | | | | | | | | Neg |
| 10 | | | | | | | | | | | | Neg |

TBRF ImmunoBlot IgG

| Antigens | Bip A (70-75kDa) | | | GlpQ | | | BpcA/fHbp | | P41/FlaB | | Vlp7 | Result |
|---|---|---|---|---|---|---|---|---|---|---|---|---|
| SEQ ID NO | 2 | 5 | 6 | 11 | 7 | 10 | 3 | 8 | 4 | 9 | 1 | |
| Sample# | Tt-2 | Pk-1 | Pk-2 | Mia | Pk | Du | Tt | Pk | Tt | Pk | Bh | |
| 1 | | | | | | | | | - | - | | Neg |
| 2 | | | | | | | | | | | | Neg |
| 3 | | Pos | | | | | | | | | | Neg |
| 4 | - | | | - | | | | | | | - | Neg |
| 5 | | | | | | Pos | Pos | | - | - | | Pos |
| 6 | | | | | | | | | | | | Neg |
| 7 | | | | | Pos | | Pos | | | | | Neg |
| 8 | Pos | | | | | | | | | | | Pos |
| 9 | | | | | | | | Pos | | Pos | | Pos |
| 10 | | | Pos | | | | | - | | | | Neg |

SPECIES-SPECIFIC ANTIGEN SEQUENCES FOR TICK-BORNE RELAPSING FEVER (TBRF) AND METHODS OF USE

FIELD OF THE INVENTION

Aspects of the present invention provide novel compositions and methods for diagnosing Tick-Borne Relapsing Fever (TBRF) resulting from infection by diverse TBRF *Borrelia* species.

SEQUENCE LISTING

The instant application incorporates by reference the Sequence Listing in the ASCII text file entitled 0153-2015US01_SL.txt, created on Jun. 17, 2022, and the size of which file is 27,304 bytes.

BACKGROUND OF THE INVENTION

Borreliosis is caused by two groups of *Borrelia*, the *B. burgdorferi* group and the Tick-Borne Relapsing Fever (TBRF) *Borrelia* group (also referred to herein as RFB (relapsing fever *Borrelia*)). The *B. burgdorferi* group was once thought to be the only group that caused Lyme-like symptoms in infected subjects, but it is now known that TBRF *Borrelia* also causes Lyme-like symptoms. Several *Borrelia* species cause TBRF, and these are usually associated with specific species of ticks. For instance, *B. hermsii* is transmitted by *Ornithodorus hermsi* ticks, *B. parkerii* by *O. parkeri* ticks, and *B. turicatae* by *O. turicata* ticks. Each tick species has a preferred habitat and preferred set of hosts. Typically, hard (*Ixodes*) ticks transmit Lyme disease pathogens whereas soft (*Ornithodorus*) ticks transmit TBRF pathogens, but there are exceptions to this rule: several RFB agents are transmitted only by hard ticks (e.g., *B. miyamotoi*) and one species, *B. recurrentis*, is louse transmitted.

The main symptoms of TBRF are high fever (e.g., 103° F.), headache, and muscle and joint aches. Symptoms can reoccur, producing a telltale pattern of fever lasting roughly three days, followed by 7 days without fever, followed by another three days of fever. Without antibiotic treatment, this process can repeat several times.

Currently, the standard for identification is by identification of TBRF spirochetes in blood smears of a subject presenting symptoms consistent with TBRF. After obtaining a blood draw, a sample must be cultured for at least 24 hours to facilitate identification. However, even early in the disease when spirochetes are highest, positive identification is only made about 70% of the time. Thus, materials and methods of the current state of the art result in a delay in diagnosis and provide a relatively low level of sensitivity and specificity. New materials and methods are needed that are suitable for the identification of TBRF causative agents with decreased assay time and increased sensitivity and specificity.

SUMMARY

The invention, in part, relates to compositions and methods that may be used to identify antibodies to infection by one or more TBRF *Borrelia* species in samples from subjects suspected of having TBRF. With compositions and methods of the present invention, identification of TBRF *Borrelia* in subject samples may be performed with greater speed, sensitivity, and specificity than with existing compositions and methods. Antigen-specific amino acid sequences of the present invention may be used in diagnostic and scientific assays. Non-limiting examples of suitable assays include immunoblots, ELISA (enzyme-linked immunosorbent assay), etc. Amino acid sequences of the present invention may be used for detecting TBRF *Borrelia* specific T-cells (e.g., the IgXSPOT test; IGeneX, Palo Alto, CA).

According to an aspect of the invention, compositions that include one or more labeled and/or tagged and/or bound amino acid sequences, wherein the one or more labeled and/or tagged and/or bound amino acid sequences comprise amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, and variants thereof which retain the immunological binding profile of FIG. 3 are provided. In some embodiments, the composition also includes amino acid sequences that are bound to a substance selected from the group consisting of nitrocellulose, nylon, polyvinylidene difluoride (PVDF), magnetic beads, and agarose. In some embodiments, each of said one or more amino acid sequences are tagged with an antibody with specificity for said amino acid sequence.

According to an aspect of the invention, methods are provided for detecting antibodies resulting from infection by one or more members of Relapsing Fever (TBRF) *Borrelia* genus, wherein the genus comprises *B. hermsii, B. turicatae, B. miyamotoi, B. duttonii,* and *B. parkeri,* if present in a sample from a subject suspected of having tick-borne relapsing fever (TBRF), the methods including: providing a biological sample obtained from a subject suspected of having TBRF; mixing the biological sample with one or more of the labeled and/or tagged and/or bound amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, and variants thereof which retain the immunological binding profile of FIG. 3; and detecting a positive immunobinding reaction which indicates the presence of TBRF specific antibodies in the sample. In some embodiments, two or more of the labeled and/or tagged and/or bound amino acid sequences are mixed with the biological sample and a sample is considered positive for TBRF if at least two amino acid sequences are detected. In some embodiments, the labeled and/or tagged and/or bound amino acid sequences are detected with anti-human IgG or anti-human IgM antibody linked to a detectable moiety. In some embodiments, the detectable moiety is selected from the group consisting of chromophores, radioactive moieties and enzymes. In some embodiments, the detectable moiety includes alkaline phosphatase. In some embodiments, the detectable moiety includes biotin.

According to an aspect of the invention, a vector including a nucleic acid sequence encoding an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, and variants thereof which retain the immunological binding profile of FIG. 3, and a heterologous nucleic acid sequence is provided. In some embodiments, the nucleic acid sequence is operatively linked to a promoter sequence. In some embodiments, the vector is a prokaryotic vector. In some embodiments, a cell includes the vector. In some embodiments, the cell is a bacterial cell.

BRIEF DESCRIPTION OF THE DRAWINGS

FIG. 3 presents a table showing representative results of TBRF ImmunoBlot IgM and IgG tests with SEQ ID NOs: 1-11 on patient serum samples. Pos, positive; I, indetermi-nate; Tt, *B. turicatae*; Pk, *B. parkeri*; Mia, *B. miyamotoi*; Du, *B. duttonii*; Bh, *B. hermsii*;

---

DESCRIPTION OF THE SEQUENCES

*B. hermsii* V1p7

SEQ ID NO: 1

Figure 1:
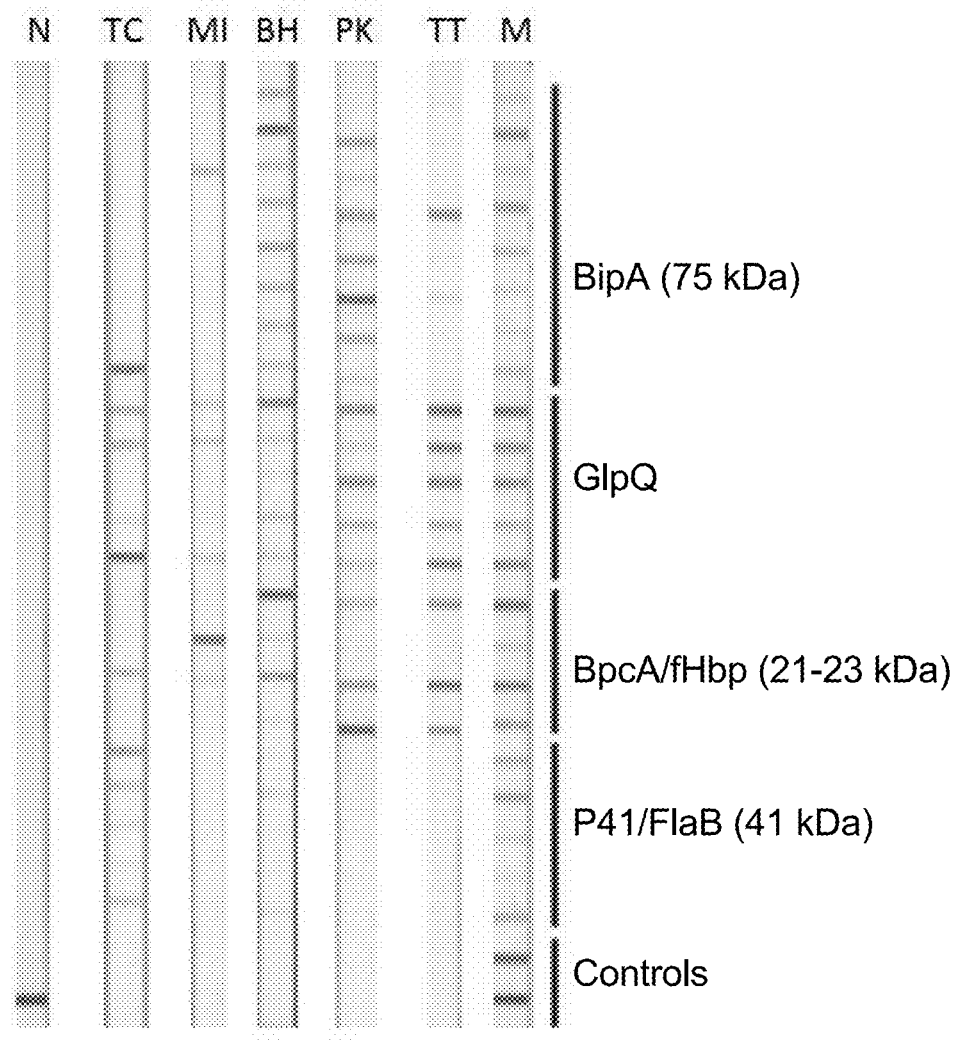
FIG. 1 shows a photomicrographic image of a line immunoblot. TBRF ImmunoBlot strips were tested with rabbit anti-TBRF *Borrelia* serum samples. Antibodies to TBRF *Borrelia* species *B. turcica, B. miyamotoi, B. hermsii, B. parkeri*. and *B. turicatae* were detected by TBRF Immuno-Blot strips prepared from recombinant antigens from all five species, demonstrating that the TBRF ImmunoBlot detected TBRF *Borrelia* group antibodies. N, negative control; TC, *B. turcica*; MI, *B. miyamotoi*; BH, *B. hermsii*; PK, *B. parkeri*, TT, *B. turicatae*; and M, positive control.

```
MQQPEAGKTGVSGGVNGNLGNSLMELGRSAENAFYAFIELVSDVLGFTAKSDTTKQ
EVGGYFNSLGAKLGEASNDLEQVAVKAETGVDKSDSSKNPIREAVNEAKEVLGTLK
GYVESLGTIGDSNPVGYANNAAGSGTTAADDELRKAFKALQEIVKAATDAGVKALK
IGATTLQANGGADNKEGAKILATSGGNPAAADVAKAAAILSSVSGEEMLSSIVKSGE
NDAQLAAAADGNTSAISFAKGGSDAHLAGANTPKAAAVAGGIALRSLVKTGKLAA
GAADNATGGGKEVQGVGVAAANKLLRAVEDVIKKTVKNVLEKAKEKIDKARGSQE
PVSESSK
```

*B. turicatae* BipA-2H

SEQ ID NO: 2

```
MDNVMSGIDNVIQGAGTFATAAMQGVGTVIDVLQDVGTFVISDIQNMGARMLFGT
GENSSVASEGSESVMSLSSNDSSEAKDVTVVLSSDVTSKGNDVAVGLSSDETQVIGR
LEKYLQSAIKINGRSDSDQSNLESGRKKFFNWLKTSDTNASKRKELVQDLQKVFDLI
KEKSSDSTELKHWVQSIVDRIEDKSTIVDIDSDDELNNDKEVDFLIENTLASRDYSGF
AVSLLFQSLADTLYDSDNNRDKSEEQIFQDLRKVFSDSSDKSEGVLGFKSKIEATN
```

*B. turicatae* BpcA/fHbp

SEQ ID NO: 3

```
MSETSLLNIETNLLNTLDDNQKQALITFKDLLQDKKHLSILEKQQKSILEDLKANQKN
YNLQDKLKKTLNSEYDKNQLNKLFDELGNIKTKQFLQQLHIILQSIKDGKPTNFASSN
FNNLNQTLEQKKEQALKYIKDKLYTDYYLYINGIQDANYFFERIMSLLE
```

*B. turicatae* P41/FlaB

SEQ ID NO: 4

```
MRNNSINAANLSKTQEKLSSGHRINRASDDAAGMGVAGKINAQIRGLSQASRNTSK
AINFIQTTEGNLNEVEKVLVRMKELAVQSGNGTYSDADRGSIQIEIEQLTDEINRIADQ
AQYNQMHMLSNKSAAQNIKTAEELGMQPAKINTPASLAGSQASWTLRVHVGANQD
EAIAVNIYAANVANLFAGEGAQVSPAQEGAQQEGVQAAPAPAAAPAQGGVNSPVN
VTTTIDANMSLSKIENAIRMVSDQRANLGAFQNRLESIKASTEYAIENLKSSYAQIQD
ATMTDEIVASTTNSILTQSAMAMIAQANQVPQYVLSLLR
```

*B. parkeri* BipA-1H

SEQ ID NO: 5

```
MDMGSTRDWLTNDDGFVRGTKGFDDSPFRRPDRVDKEVSAGGREIEKAFSRNLGV
AGGQRKGTDDVKNGIAGARESGGVLKEAENAGQRDVDDSGEGIKNDVIQNLGSVG
VQVAVGSENNGDDSGQEAEKGSQNLGDTGTQRVVSTSDLNSHLGVESKGGMSTNK
EGISTNHVTENRNSINSITSTSSGLSTALQIAGTSTRASGYEGEVTTNAQDRSFIDTKTQ
DSKKQYSDFSDQDIRDKILGNVVGGVV
```

*B. parkeri* BipA-2H

SEQ ID NO: 6

```
MGNVMSGIDNVIQGAGTFATAAMQGVGTVIDVLQDVGTFVISDIQNMGARMFFGT
GESSSVASEDSESVMSLSSKASSEAKDTTVGLSSDVTSKGNNVAVGLSSDEIQIIGRLE
KYLKSAIKINGRSDSDQSKLESGHKKFFQWLKTSDTNASKRKELVQNLQRVFNLIKE
KSSDSTELKKWMQSIVDDIENKSTIIDINSDDKLNNDKEVDFLIEKTLGSSDYSGFAVS
LLFQALADTLYDSENSRDKSEEQIFKDLRKVFSDKSEGVLEFKSKIEATN
```

*B. parkeri* GlpQ

SEQ ID NO: 7

```
MCQNEKMSMTNKKSPLTIAHRGASGYLPEHTLESKAFAYALGADYLEQDIVLTKDN
VPIIMHDPELDTTTNVAKLFPERARENGRYYSVDFTLDELKSLSLSERFDLETRKPIYP
KRFPLNEYNFKIPTLEEEIQFIQGLNKSTGRNVGIYPEIKKPLWHKQQGKDISKIVIEIL
NKYGYKSKEDKIYLQTFDFDELKRIREELGYQGKLIMLVGENDWNEAPTDYEYIKSQ
EGMTEVAKYADGIGPWIPQIIIDGKITDLTSLAHKYNMEVHAYTFRIDSLPSYVKDAN
ELLDLLFNQAKIDGLFTDFTDTVVKFIKQ
```

-continued

DESCRIPTION OF THE SEQUENCES

*B. parkeri* BpcA/fHbp

SEQ ID NO: 8

```
MSETSLLNTLDNNQKQALITFKDLLQDKNHRSILEKQQKSILKDLEKHQENSNLQDK
LKKTLNSEYDKTQLNKLFDELGNIKTKQFLQKLHIMLKSINNGTLTSFSSSNFKDSNQ
TLEQKKEQALQYIKGQLYTDYYLYINGIQDANYFFERIMSVLEI
```

*B. parkeri* P41/FlaB

SEQ ID NO: 9

```
MRNNSINAANLRKTQEKLSSGHRINRASDDAAGMGVAGKINAQIRGLSQASRNTSK
AINFIQTTEGNLNEVEKVLVRMKELAVQSGNGTYSDADRGSIQIEIEQLTDEINRIADQ
AQYNQMHMLSNKSAAQNIKTAEELGMQPAKINTPASLAGAQASWTLRVHVGANQ
DEAIAVNIYASNVANLFAGEGAQVSPAQEGAQQEGVQAAPAPAAAPAQGGVNSPV
NVTTTVDANMSLSKIENAIRMVSDQRANLGAFQNRLESIKASTEYAIENLKSSYAQIK
DATMTDEIVASTTNSILTQSAMAMIAQANQVPQYVLSLLR
```

*B. duttonii* GlpQ

SEQ ID NO: 10

```
MENAKINKKSALHAHRGASGYLPEHTLEAKAYAHALGADYIEQDIVLTKDDIPIVMH
DPELDTTTNVAKLFPGRARENGKYYSVDFTLAEIKSLSLSERFDPETQQPIYPNRFPAT
EYDFKIPTLEEEIKFIQGLNKSTGKNIGIYPEIKKPLWHKQQGKDISKIVIDILNKYGYK
SKEDKIYLQTFDFDEIKRIREELGYQGKLIMLVGENDWEEAPTDYEYIKSEEGMAEV
AKYADGIGPWIPQIIINGQITGLISLAHKYNMQVHPYTFRIDALPSYVKDPNELLELLFI
KAKVDGLFTDFVDISIKFMQ
```

*B. miyamotoi* GlpQ

SEQ ID NO: 11

```
MASMTGGQQMGRGSEMGENKKSPLIIAHRGASGYLPEHTLEAKAYAYALGADYLE
QDIVLTKDNIPVIMHDPEIDTTFNVAQLFPNRARENGRYYATDFTLTELKSLNLSERF
DPENKKPIYPNRFPLNEYNFKIPTLEEEIQFIQGLNKSTGKNVGIYPEIKKPFWHKQQG
IKDISKIVIEILNKYGYKSKEDKPILQTFDFDELKRIRKELGYQGKLIMLVGENDWNEA
VIDYEYIKSEEGIAEVAKYSDGIGPWIPQIIMGKITELTNIAHKYNIEVHPYTFICIDAL
PSYVKNENELLDLLFNKAKVDGIFTDFTDTVMNFIKK
```

DETAILED DESCRIPTION OF THE INVENTION

The RFB species best known for causing TBRF in the United States of America (USA) are *B. hermsii. B. miyamotoi. B. parkeri*, and *B. turicatae*. However, other RFB species that cause TBRF continue to be identified. For example, a patient infected with *B. johnsonii*-like species, previously found only in bat ticks, was identified in Wisconsin. Moreover, TBRF has also been reported in Central and South America. *B. hispanica, B. persica*, and *B. miyamotoi* are important causes of TBRF in Europe and Asia, and *B. hispanica, B. crocidurae*, and *B. duttonii* are important causes of TBRF in Africa. Although most RFB species are transmitted by soft ticks of the genus *Ornithodoros, B. miyamotoi* may be transmitted by the same hard ticks of the genus *Ixodes* that transmit Lyme Disease *Borrelia* (LDB) species. Other RFB species, *B. lonestari*. the recently described *B. turcicia*, and *B. tachyglossi*. are members of a rapidly expanding *Borrelia* clade associated with reptile (*B. turcica*) or echidna (*B. tachyglossi*) hosts and are also transmitted by hard ticks. In order to provide timely treatment, clinicians must be able to rapidly and correctly identify whether a patient presenting with symptoms of tick-borne disease have been exposed to TBRF species.

Aspects of the invention provide a method of quickly and accurately detecting *Borrelia* antisera in a sample from a subject suspected of having TBRF. A subject suspected of having TBRF can be identified as having symptoms such as a high fever (e.g., 103° F.), headache, and muscle and joint aches. Symptoms typically reoccur, producing a telltale pattern of fever lasting roughly 3 days, followed by approximately 7 days without fever, followed by another 3 days of fever. Without proper antibiotic treatment, this process can repeat several times. Since the symptoms of TBRF can mimic, for example, viral flu-like symptoms, accurate diagnosis of TBRF is important for providing an effective treatment for the subject. The present invention provides a quick and easy diagnostic test for detecting the presence of antibodies specific for causative *Borrelia* species, thereby satisfying the need for such a test.

Because TBRF can be caused by several RFB species, and because geographic ranges of RFB species may overlap, tests for RFB species need to be inclusive—that is, a test needs to be able to detect antibodies to multiple species concurrently. The present invention provides for antigenic amino acid sequences specific for various TBRF *Borrelia* species. The amino acid sequences of the present invention encode antigenic peptides that have high specificity and/or sensitivity for the indicated genus. The inclusion of antigenic peptides that exhibit cross-reactivity across *Borrelia* species boundaries is also important with respect to the development of inclusive serological, or other immunologically-based assays, wherein the goal is to detect infection, not necessarily to identify a particular species responsible for infection. For example, the disclosure includes multi-panel immunoassays wherein, in the context of a single test screen, multiple RFB species are detectable.

The present invention provides novel compositions and methods for diagnosing infection by TBRF *Borrelia* species. The invention is based, in part, on the discovery of species-specific amino acid sequences encoding antigenic peptides (which may also be referred to in the art as peptide antigens or antigens), as described herein.

The present invention, in one aspect, is a composition comprising one or more labeled and/or tagged and/or bound amino acid sequences, wherein the one or more labeled and/or tagged and/or bound amino acid sequences have at least 90%, 95%, 98%, 99%, 99.5%, or 100% homology to SEQ ID NO: 1, SEQ ID NO: 2, SEQ ID NO: 3, SEQ ID NO:

4, SEQ ID NO: 5, SEQ ID NO: 6, SEQ ID NO: 7, SEQ ID NO: 8, SEQ ID NO: 9, SEQ ID NO: 10, and SEQ ID NO: 11. Sequences with less than 100% homology may be modified with one or more substitutions, deletions, insertions, or other modifications with respect to the amino acid sequences provided herein. Exemplary modifications include, but are not limited to conservative amino acid substitutions, which will produce molecules having functional characteristics similar to those of the molecule from which such modifications are made. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly-sized negatively-charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). One of ordinary skill in the art can determine if sequences with less than 100% homology can bind naturally- or non-naturally-occurring TBRF-related antibodies, as well as the sensitivity and specificity of the antibody to the modified sequences. One of ordinary skill in the art will be able to identify sequences with significant homology to SEQ ID NOs: 1-11 of the present invention that give acceptable or equivalent responses in the methods of the present invention without undue experimentation, in view of the teachings of this specification.

In some embodiments, the present invention is a composition comprising one or more labeled and/or tagged and/or bound amino acid sequences, wherein the one or more labeled and/or tagged and/or bound amino acid sequences comprise amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, and variants thereof which retain the immunological binding profile of FIG. 3. As used herein, "consisting of", when used as a claim transition referring to an amino acid sequence, refers to amino acid sequences having 100% homology to the specified amino acid sequence (i.e., SEQ ID NOs: 1-11).

Aspects of the present invention provide antigen-specific amino acid sequences for TBRF *Borrelia* specific species. These novel amino acid sequences may be used in assays to identify TBRF specific *Borrelia* in samples from subjects suspected of having TBRF. With the amino acid sequences of the present invention, identification of TBRF *Borrelia* in subject samples is performed with greater speed, sensitivity and specificity than other current methods. The amino acid sequences of the present invention may be used in diagnostic and scientific assays. Non-limiting examples of suitable assays include immunoblots, line immunoblots, ELISA (enzyme-linked immunosorbent assay), etc. The amino acid sequences of the present invention may be used for the detection of TBRF *Borrelia* specific T-cells, for example, with the IgXSPOT test (IGeneX, Milpitas, CA).

In some embodiments, the invention is a composition comprising one or more labeled and/or tagged and/or bound amino acid sequences, wherein the one or more labeled and/or tagged and/or bound amino acid sequences comprise amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, and variants of those sequences. The expression "variants" encompasses any modification(s) of a specified amino acid sequence (i.e., SEQ ID NOs. 1-11) which retain(s) the immunological binding profile of FIG. 3. Such modifications may include insertions and deletions (internal or from the N- or C-terminus, or both).

Nucleic acid sequences, including polynucleotides and oligonucleotides, encoding the amino acid sequences of the present invention, and portions thereof, may be expressed in cultured cells to provide isolatable quantities of peptides displaying biological (e.g., immunological) properties of the antigenic peptide encoded by the amino acid sequences of the present invention. Because of redundancy of the genetic code, multiple nucleic acid sequences may be suitable for the production of the peptide sequences of the present invention. One of ordinary skill in the art will be able to determine one or more nucleic acid sequences for production of the amino acid sequences of the present invention. A nucleic acid sequence encoding an amino acid sequence of the present invention may be labeled by any suitable label known to one of ordinary skill in the art.

In this regard, nucleic acid sequences suitable for the production of the amino acid sequences of the present invention may be substantially homologous to naturally occurring sequences. Substantial homology of a nucleic acid sequence as used herein means that: (a) there is greater than 65%, 75%, 85%, 95%, 98%, or 99% homology with the naturally occurring sequence, or (b) the homologous nucleic acid sequence will hybridize to the compared sequence or its complementary strand under stringent conditions of the temperature and salt concentration. These stringent conditions will generally be a temperature greater than about 22° C., usually greater than about 30° C. and more usually greater than about 45° C., and a salt concentration generally less than about 1 M, usually less than about 500 mM, and preferably less than about 200 mM. The combination of temperature and salt concentration is more important in defining stringency than either the temperature or the salt concentration alone. Other conditions which affect stringency include GC content of the compared sequence, extent of complementarity of the sequences, and length of the sequences involved in the hybridization, as well as the composition of buffer solution(s) used in the hybridization mixture. These and other factors affecting stringency are well described in the scientific and patent literature. One of ordinary skill in the art will be able to determine suitable conditions for determining the homology of the nucleic acid sequences encoding the antigenic peptides of the present invention.

Homologous nucleic acid sequences may be determined based on the nature of a nucleotide substitution in the nucleic acid sequence. For example, synonymous nucleotide substitutions, that is, nucleotide changes within a nucleic acid sequence that do not alter the encoded amino acid sequence, will be better tolerated and, therefore, may be more numerous in a particular nucleic acid sequence than non-synonymous nucleotide substitutions. One of ordinary skill in the art will be able to determine the suitable number and location of substitutions that may be allowed in a nucleic acid sequence that encodes an amino acid sequence of the present invention without adversely affecting the antigenicity of the encoded antigenic peptide, without undue experimentation.

Labels and Tags

One or more amino acid sequences of the invention may be labeled and/or tagged and/or bound. As used herein, a "label" or "tag" is a detectable moiety that may be attached to an amino acid sequence of the invention. A label or tag may be covalently or non-covalently attached to an amino acid sequence of the invention. Non-limiting examples of such "tags" are natural and synthetic (i.e., non-naturally occurring) nucleic acid and amino acid sequences (e.g., poly-AAA tags), antibodies and detectable moieties such as labels (discussed elsewhere herein). Thus, the definitions of the phrases "labeled" and "tagged" may have overlap in that a tag may also, in some instances, function as a label. Furthermore, tags useful with the present invention may be linked to a label.

The amino acid sequences of the present invention, or any tags attached to an amino acid sequence of the present invention, may be labeled with any suitable label known to one of ordinary skill in the art. Such labels may include, but are not limited to, biotin/streptavidin, enzyme conjugates (e.g., horseradish peroxidase (HRP), alkaline phosphatase (AP), glucose oxidase, and β-galactosidase), fluorescent moieties (e.g., FITC, fluorescein, rhodamine, etc.), biological fluorophores (e.g., green fluorescent protein (GFP), R-phycoerythrin) or other luminescent proteins, etc. Any suitable label known to one of ordinary skill in the art may be used with the present invention.

In some embodiments, amino acid sequences of the invention may be "bound." A "bound" amino acid sequence is an amino acid sequence that has been immobilized in order to permit the use of the amino acid sequence in a biological test such as, for example, an immunoassay. In the context of the present invention, a "bound" amino acid sequence is an amino acid sequence attached (e.g., covalently or non-covalently bound, etc.) directly or indirectly to a non-natural surface or substance. Additionally or alternatively, "bound" amino acid sequences of the present invention may be attached, directly or indirectly, to a natural surface or substance, either of which is not naturally associated with the amino acid sequence. Non-limiting examples of substances to which the amino acid sequences of the present invention may be bound are nitrocellulose, nylon, polyvinylidene difluoride (PVDF) plastics, metals, magnetic beads and agarose (e.g., beads). Linking agents known to those of ordinary skill in the art may be used to aid or enhance binding of the amino acid sequences of the present invention to a surface or substance.

Production of Amino Acid Sequences

In some embodiments, amino acid sequences of the invention may be non-natural, synthetic sequences, such as sequences produced by recombinant technology or sequences synthesized by protein synthesizing apparatuses. As such, the amino acid sequences of the present invention may be produced by recombinant technology, as is described and enabled in the literature and in commonly referred to manuals such as, e.g., Short Protocols in Molecular Biology, Second Edition, F. M. Ausubel, Ed., all John Wiley & Sons, N.Y., edition as of 2008; and, Sambrook, et al., Molecular Cloning: A Laboratory Manual, 3rd ed., Cold Spring Harbor Laboratory Press, Cold Spring Harbor, 2001, and as is well known to one of ordinary skill in the art. In one embodiment, the amino acid sequences of the present invention are made recombinantly in *E. coli.*

As used herein, the term "vector" refers to a nucleic acid molecule capable of transporting between different genetic environments another nucleic acid to which it has been operatively linked. In addition to the nucleic acid sequence encoding an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, and variants thereof which retain the immunological binding profile of FIG. 3, the vectors of the present invention also include a heterologous nucleic acid sequence. As used herein, heterologous refers to a nucleic acid sequence that does not naturally occur in the organism from which the Markush group sequences are derived. The term "vector" may also refer to a virus or organism that is capable of transporting the nucleic acid molecule. One type of vector is a plasmid, a small, circular, double-stranded, extrachromosomal DNA molecule that is physically separate from and can self-replicate independently from chromosomal DNA. Some useful vectors are those capable of autonomous replication and/or expression of nucleic acids to which they are linked. Vectors capable of directing the expression of nucleic acids to which they are operatively linked are referred to herein as "expression vectors." Other useful vectors, include, but are not limited to bacterial plasmids and bacterial artificial chromosomes (BACs), cosmids, and viruses such as lentiviruses, retroviruses, adenoviruses, and phages.

Vectors useful in methods of the invention may include additional sequences including, but not limited to, one or more signal sequences and/or promoter sequences, or a combination thereof. Promoters that may be used in methods and vectors of the invention include, but are not limited to, cell-specific promoters or general promoters. Non-limiting examples of promoters that can be used in vectors of the invention are: ubiquitous promoters, such as, but not limited to: CMV, CAG, CBA, and EF1a promoters. Methods to select and use suitable promoters are well known in the art.

Vectors useful in methods of the invention may be used to express a fusion protein comprising sequences of the invention in a cell. Expression vectors and methods of their preparation and use are well known in the art. In some embodiments of the invention, a nucleic acid sequence of an expression vector encodes a fusion protein comprising an amino acid sequence of the invention. It is well known in the art how to prepare and utilize fusion proteins that comprise a polypeptide sequence. In some embodiments, a fusion protein comprising an amino acid sequence of the invention may also include an epitope tag that may be used for purification of the fusion protein or in a method of the invention. Non-limiting examples of epitope tags are a FLAG tag, a fluorescent tag (including but not limited to green fluorescent protein (GFP)), a GST tag, a hemagglutinin (HA), a poly-histidine (poly-His) tag, a Myc tag, an MBP tag, or a V5 tag. In some embodiments, a fusion protein comprising an amino acid sequence of the invention may also include a detectable label, as described elsewhere herein.

Subjects and Cells

As used herein, a subject may be an animal, such as a mammal or a non-mammal. Non-limiting examples of mammalian subjects include primates (including but not limited to humans), rodents (including but not limited to mice, rats, squirrels, chipmunks, prairie dogs), lagomorphs, deer, canids (including but not limited to dogs, foxes, coyotes, and wolves), felids (including but not limited to domestic cats, bobcats, cougars, and other wild cats), bears, horses, cows, sheep, goats, and pigs. Non-limiting examples of non-mammalian subjects include birds, amphibians, lizards, insects, and arthropods. As used herein, a cell may be a bacterial cell, including but not limited to *E. coli*, or an animal cell, either mammalian or non-mammalian.

Assays and Methods of Detection

Amino acid sequences of the invention may be tagged with an antibody with specificity for any of said amino acid sequences. Specificity for said amino acid sequence, i.e., antibody specificity, is the property of antibodies which enables them to react preferentially with some antigenic determinants and not with others. Specificity is dependent on chemical composition, physical forces and molecular structure at the binding site. Sensitivity is how strongly the antibody binds to the antigenic determinant. One of ordinary skill in the art can determine specificity and sensitivity of an antibody for a particular amino acid sequence using standard affinity assays, such as immunoblotting, Ouchterlony assays, titer assays, etc. In another aspect, the present invention provides a method of quickly and accurately detecting TBRF *Borrelia* antisera in a sample from a subject suspected of having TBRF. The method of the present invention for detecting TBRF *Borrelia* antisera in a sample from a subject suspected of having TBRF, may comprise, for example, providing a biological sample (including but not limited to blood, saliva) obtained from a subject suspected of having TBRF, mixing the biological sample with one or more of the labeled and/or tagged and/or bound amino acid sequences of the present invention and detecting a positive reaction which indicates the presence of Lyme disease antisera in the sample. The antisera may be detected by, for example, immunoblotting, ELISPOT, ELISA, Western blotting, lateral flow assay, or any other appropriate immunoassay known to one of ordinary skill in the art. These techniques are known to one of ordinary skill in the art and procedures can be found in common technical references. While similar, each of these techniques has its advantages and disadvantages. Other suitable techniques may be known to those of skill in the art and are incorporated herein.

To assess the impact of testing limitations and to determine levels of exposure to TBRF *Borrelia*, a modified Western blot procedure, the line immunoblot, was developed and employed in aspects of the invention described herein. A line immunoblot uses recombinant antigens from common strains and species of the TBRF *Borrelia* complex for serological identification and diagnosis of TBRF in serum from patients with a suspected tick-borne disease. As described elsewhere herein, the serotype makeup of TBRF *Borrelia* exposure may be more complex than has been previously acknowledged, and infection with more than one TBRF *Borrelia* species is possible.

Western blotting can involve separating proteins by electrophoresis and then transferring to nitrocellulose or other solid media (e.g., polyvinylidene fluoride or PVDF-membrane and nylon membrane), and is described in more detail below. Immunoblotting can also involve applying proteins to a solid media manually or by machine. Preferably, the proteins are applied in straight lines or spots and dried, binding them to the solid support medium, e.g., nitrocellulose. The proteins used in an immunoblot can be isolated from biological samples or produced by recombinant technology, as is well known by those of ordinary skill in the art. The bound proteins are then exposed to a sample or samples suspected of having antibodies specific for the target proteins. With this procedure, a known antibody can be used to determine if a protein is present in a sample, such as when the proteins of lysed cells are separated by electrophoresis and transferred to the solid medium. Western blotting allows for the identification of proteins by size as well as by specificity for a specific antibody.

Similarly, with a procedure called immunoblotting, known proteins can be bound to the solid medium and samples, such as samples from subjects suspected of having an infection, can be tested for the presence of specific antibodies in the sample by contacting the bound protein with the sample. An antibody that binds the target protein is usually referred to as the primary antibody. A secondary antibody, specific for conserved regions of the primary antibody (for example, a rabbit-anti-human IgG antibody may be used to detect primary human antibodies) is used to detect any bound primary antibodies. The secondary antibody is usually labeled with a detectable moiety for visualization. Non-limiting examples of suitable labels include, for example, chromophores such as biotin, radioactive moieties and enzymes such as alkaline phosphatase, etc. The use of these and other materials for the visualization of antibodies are well known to one of ordinary skill in the art.

The Enzyme-Linked ImmunoSpot (ELISPOT) method can detect human T-cells that respond to Lyme-specific antigens in vitro. In an ELISPOT assay, the surfaces of PVDF membrane in a 96-well microtiter plate are coated with capture antibody that binds, for example, anti-Interferon gamma (IFNγ) or other cytokine-specific antibody. During the cell incubation and stimulation step, the T-cells isolated from patient whole blood are seeded into the wells of the plate along with aforementioned sequence(s), and form substantially a monolayer on the membrane surface of the well. Upon stimulation of any antigen-specific cells with one or more of the sequences of the present invention they are activated and they release the IFNγ, which is captured directly on the membrane surface by the immobilized antibody. The IFNγ is thus "captured" in the area directly surrounding the secreting cell, before it has a chance to diffuse into the culture media, or to be degraded by proteases and bound by receptors on bystander cells. Subsequent detection steps visualize the immobilized IFNγ as an ImmunoSpot; essentially the secretory footprint of the activated cell.

For a specific example of an ELISPOT test, each well of the plate is coated with a purified cytokine-specific antibody specific for the test or cell being detected. T-cells are isolated from a subject (for example, a subject suspected of having Lyme Disease or TBRF) and cultured in each well and stimulated with recombinant antigens of one or more sequences of the present invention. Lyme-positive patient cells secrete cytokine in response to stimuli, which is captured by the antibody coated in the well and further detected by ELISA.

ELISA assays may also be used to detect antigens. ELISA assays permit quantification of a specific protein in a mix of proteins (for example, a lysate) or may be used to determine if a peptide is present in a sample. Likewise, ELISA assays may be used to determine if a specific antibody is present by using a specific antigen as a target. As used with the present invention, target amino acid sequence(s) are attached to a surface. Then, if present in the sample being tested, the reactive antibody can bind to the antigen. A secondary antibody linked to an enzyme is added, and, in the final step, a substance containing the enzyme's substrate is added. The subsequent reaction produces a detectable signal, most commonly a color change in the substrate.

Lateral flow assays, also referred to by a variety of other names that include but are not limited to lateral flow tests, lateral flow devices, lateral flow immunoassays, lateral flow immunochromatographic assays, and rapid tests, are simple, versatile, paper-based platforms for detecting and/or quantifying the presence of one or more analytes, such as an antigen, in a mixture, such as a liquid sample. Lateral flow assays may be qualitative or quantitative. In a lateral flow assay, a sample containing one or more analytes of interest is applied to an adsorbent sample pad and is drawn via capillary action through various zones of polymeric test strips to which are attached molecules that can interact with the analyte(s). The sample migrates to the conjugate release pad, which contains molecules that specifically bind to the analyte(s) of interest and are conjugated to fluorescent, colored, or otherwise detectable particles. Finally, the sample, including the bound analyte(s) migrates into the detection zone. Within the porous membrane of the detection zone are biological components such as antibodies or antigens, that are immobilized in lines and that will react with the detectable particles. Lateral flow assays typically have a control line for confirming sample flow through the strip and one or more test lines for detecting the presence of the analyte(s) of interest. The results may be read by eye or with a machine capable of reading and interpreting the results. A lateral flow assay may be designed as a direct or "sandwich" assay, in which the presence of a colored line at the test line position indicates a positive test, or as a competitive assay, in which the absence of a colored line indicates a positive test. Direct and competitive assays may be multiplexed.

In one aspect of the method of the present invention, a positive result is indicated when two or more of the labeled and/or bound amino acid sequences of the present invention are mixed with the biological sample and when at least two amino acid sequences are detected. In another aspect of the invention, a positive result is indicated when at least one of the labeled and/or bound amino acid sequences of the present invention are mixed with the biological sample and when at least one amino acid sequence is detected.

In the method of the present invention, any primary antibody bound to a peptide encoded by an amino acid sequence of the present invention may be detected with anti-human antibodies, such as IgG or IgM, used as the secondary antibody conjugated to a detectable moiety. As described elsewhere herein, the detectable moiety may be selected from the group consisting of chromophores, radioactivity moieties and enzymes or other detectable moiety known to one of ordinary skill in the art. In one embodiment, the detectable moiety comprises alkaline phosphatase. In another embodiment the detectable moiety comprises biotin.

In another aspect of the invention, a method is provided for detecting and distinguishing various species of *Borrelia* in a sample. The sample may be from a subject suspected of having Lyme disease. The method may comprise, for example, providing a sample, for example, a biological sample obtained from a subject suspected of having TBRF and mixing or contacting the biological sample with one or more of the labeled and/or bound amino acid sequences of the present invention. Amino acids may be labeled to confirm their presence if positive results are not obtained in the assay.

In some embodiments of the invention, a sample may be considered positive in a multi-species panel assay for TBRF *Borrelia* if at least one amino acid sequence is detected. In some embodiments of the invention, a sample may be considered positive in a multi-species panel assay for TBRF *Borrelia* if at least two amino acid sequences are detected. In some embodiments of the invention, a sample may be considered positive for a specific species of TBRF *Borrelia* if at least two amino acid sequences identified with a species are detected.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

EXAMPLES

Example 1. TBRF ImmunoBlot Antigen Inclusivity Study

TBRF ImmunoBlot IgG and IgM tests, qualitative immunoblot assays, were designed and performed to detect IgG and IgM antibodies directed against TBRF *Borrelia* species in serum samples suspected of having Relapsing Fever or Lyme-like symptoms. Recombinant TBRF *Borrelia* antigens were sprayed as straight lines onto nitrocellulose strips, which were then used in the TBRF ImmunoBlot Test. Experiments were undertaken to determine the specificity of the TBRF ImmunoBlot Test.

Methods

Antigen Preparation

Recombinant target proteins were obtained by cloning hybrid gene constructs or portions of genes into pET vectors, expressing the gene products in *Escherichia coli* (GenScript, Piscataway, NJ), then isolating the proteins to >90% purity, as previously described [Liu et al., *Healthcare* (2018) 6(3) pii: E99; Shah et al., *Healthcare* (2019) 7:121]. Recombinant proteins from several TBRF *Borrelia* species (*B. hermsii, B. miyamotoi, B. turicatae* and *B. turcica*) were derived for the detection of four target antigens: BipA, GlpQ, BpcA/fHbp and P41/FlaB, as previously described [Shah et al., *Healthcare* (2019) 7:121].

Preparation of Antigen Strips

Antigen strips for TBRF immunoblots were prepared as previously described [Liu et al., *Healthcare* (2018) 6(3) pii: E99; Shah et al., *Healthcare* (2019) 7:121]. Purified proteins and control proteins were diluted (7-19 ng protein/line) and sprayed in straight lines on nitrocellulose sheets (Cytiva, Marlborough, MA) using a BioDot liquid dispenser (BioDot, Irvine, CA). The sheets were then blocked with 5% non-fat dry milk and sliced into 3 mm wide strips.

Detection of Antibody Reactivity

Serological immunoblot testing was performed at IGeneX Reference Laboratory, a high-complexity testing facility with Clinical Laboratory Improvement Amendments (CLIA) certification.

Reactivity between TBRF *Borrelia*-specific antibodies from test sera and TBRF *Borrelia* antigens on immunoblots was detected as previously described [Liu et al., *Healthcare* (2018) 6(3) pii: E99; Shah et al., *Healthcare* (2019) 7:121]. Strips were labeled, soaked in diluent (100 mM Tris, 0.9% NaCl, 0.1% Tween-20, and 1% non-fat dry milk) for 5 minutes (min) in a trough; then, a 10 µL aliquot of either test serum or control serum was added to the strip. Strips with sera were incubated at room temperature for one hour, washed three times with wash buffer (KPL, Gaithersburg, MD) at room temperature, and the final wash solution was then aspirated. To detect IgG and IgM reactivity, strips were incubated with alkaline phosphatase-conjugated goat anti-human IgG at 1:10,000 dilution or IgM at 1:6,000 dilution, respectively (KPL, Gaithersburg, MD), for one hour, and then washed three times. To visualize bands of antibody/antigen reactivity, the strips were reacted with a chromogenic substrate, 5-bromo-4-chloro-3-indolylphosphatenitro-blue tetrazolium (BCIP/NBT, KPL, Gaithersburg, MD), and the reaction was terminated by washing with distilled water after the calibration control produced a visible band at 39 kDa. Bands demonstrating an intensity lower than that of the calibration control were reported as negative. Human sera from patients with confirmed *Borrelia* infection were used as positive controls and sera from uninfected persons were used as negative controls. All immunoblot testing of patient samples was performed with simultaneous testing of positive and negative control serum samples.

Scoring of Immunoblots

For TBRF *Borrelia* ImmunoBlots, detection of either IgG or IgM antibodies against P41/FlaB (41 kDa), as well as any two out of the four antigens BipA (75 kDa), GlpQ, BpcA/fHbp (21-23 kDa) gave the best specificity for TBRF species.

Detection of either IgG or IgM antibodies to two or more proteins within each antigen type was regarded as a positive reaction for that antigen type. Applying the same criteria for reactivity of either IgM or IgG antibodies to the four TBRF

*Borrelia* antigens led to optimum sensitivity of detection, as previously described [Shah et al., *Healthcare* (2019) 7:121].

Results

As shown in FIG. 1, antibodies to TBRF *Borrelia* species *B. turicica, B. miyamotoi, B. hermsii, B. parkeri,* and *B. turicatae* species were detected by the TBRF ImmunoBlot strip prepared from recombinant antigens from all five species, indicating that TBRF ImmunoBlots detected TBRF *Borrelia* group antibodies.

Example 2. TBRF ImmunoBlot Clinical Study of Patients with Suspected Tick-Borne Disease A study of patients who met the case definition of Chronic Lyme Disease (CLD) was performed to assess the impact of testing limitations and to determine levels of exposure to TBRF *Borrelia*. The results also revealed that all had exposure to *B. burgdorferi* species.

Methods

Methods used were as described in Example 1 and elsewhere herein.

Antigen Preparation and Preparation of Antigen Strips

Additional recombinant proteins from several TBRF *Borrelia* species (*B. hermsii, B. miyamotoi, B. turicatae, B. parkeri,* and *B. duttonii*) were derived as described elsewhere herein for the detection of target antigens BipA, GlpQ, BpcA/fHbp, P41/FlaB, and Vlp7. These recombinant proteins, comprising the amino acid sequences of SEQ ID NOs: 1-11, were included on TBRF ImmunoBlot strips.

Clinical Testing

A total of 265 patient serum samples were tested by TBRF ImmunoBlots IgM and IgG, including 90 patients with CLD symptoms and 212 patient serum samples that were negative for TBRF.

Chronic Lyme Disease Patient Cohort (n=90)

A patient cohort of 90 patients with CLD was recruited from a medical practice located in San Francisco, CA, specializing in the diagnosis and treatment of tick-borne diseases. The Western Institutional Review Board (WIRB), Puyallup, WA approved the anonymous retrospective data collection protocol and consent form. Patients of either sex qualified for the study provided they were at least 18 years of age, had a medical history of musculoskeletal, neuropsychiatric and/or cardiac symptoms consistent with LD, and gave written informed consent for data collection. Subjects were included in the study if they met the case definition of untreated or previously treated CLD with symptoms lasting more than six months, as described in detail elsewhere [Cameron et al., *Expert Rev Anti Infect Ther*. (2014) 12:1103-1135; Stricker et al., *Am J Infect Dis* (2018) 14:1-44]. Patients were not required to have had a documented tick bite or erythema migrans rash for participation in the study because serological testing was used to detect exposure rather than active infection. De-identified patient samples were coded according to the patient's place of residence. Blood was drawn and serum was separated at independent laboratories including BioReference®, LabCorp®, and AnyLabTestNow®, and serum samples were transported to the reference laboratory for immunoblot testing.

Control Patients (n=175)

A total of 175 human sera expected to be negative for *B. burgdorferi* species and TBRF *Borrelia* species were obtained from the Centers for Disease Control and Prevention (CDC, Atlanta, GA), College of American Pathologists, New York State Department of Health, New York Biologics (Southampton, NY, USA) and IGeneX Reference Laboratory (Milpitas, CA, USA). The IGeneX samples were left-over sera received for routine testing for tick-borne diseases that would otherwise have been discarded. ImmunoBlot IgM and IgG testing of patient sera and control sera was performed by laboratory personnel in a blinded fashion in the same manner as testing of clinical samples from TBRF patients. Results are shown in Tables 1-2 and FIGS. 2-3.

Results

Figure 2:
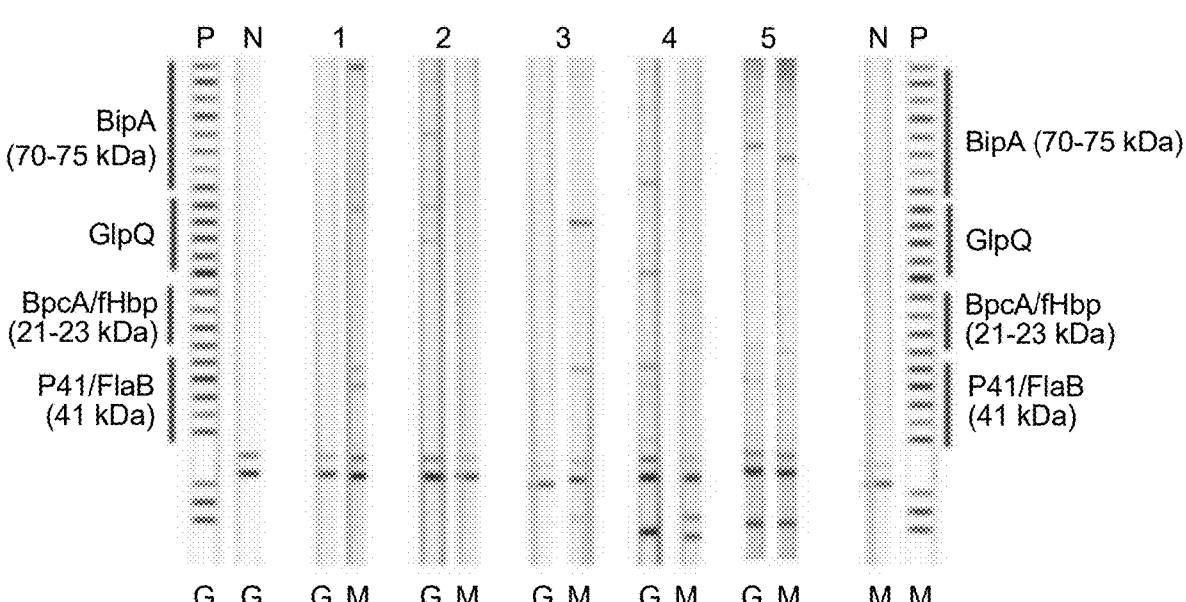
FIG. 2 shows a photomicrographic image of TBRF Immu-noBlots of representative patient serum samples. Patient serum samples were tested on Tick-Borne Relapsing Fever (TBRF) IgM and IgG ImmunoBlots. These results illustrate how detection of antibodies to TBRF *Borrelia* species identified patients with Chronic Lyme Disease symptoms that would otherwise have been missed by only testing for *Borrelia burgdorferi* species antigens. P, positive control; N, negative control; G, TBRF ImmunoBlot IgG; M, TBRF ImmunoBlot IgM; 1, *B. hermsii*-positive IgM; 2, *B. turica-tae*-positive IgG; 3, *B. miyamotoi*-positive IgM; 4, *B. tur-cica*-positive IgG; 5, *B. parkeri*-positive IgM and IgG.

Immunoblot reactivity for TBRF *Borrelia* in representative patient serum samples is shown in FIG. 2, demonstrating that TBRF ImmunoBlots successfully detect TBRF *Borrelia* group antibodies in serum samples.

The results obtained with the 175 control sera that were expected to be negative for *B. burgdorferi* species and RFB yielded a false positive rate of 2.3% (4/175 samples) for the *B. burgdorferi* species immunoblot and 2.9% (5/175 samples) for the RFB immunoblot (Table 1). False positive tests for RFB were seen with an allergy patient serum (one control), multiple sclerosis (one control), viral infection (one control), and syphilis (two controls).

Using the TBRF ImmunoBlot test described in Example 1 and including SEQ ID NOs: 1-11, the study of patients who met the CLD case definition revealed that all had exposure to *B. burgdorferi* species, and 62% had exposure to TBRF species. In the CLD cohort (Table 2), ImmunoBlot testing revealed that out of the 90 subjects with suspected LD, a total of 48 patients (53%) were seropositive for TBRF alone, and 8 patients (9%) had mixed infection with TBRF *Borrelia* species and *B. burgdorferi* species. FIG. 2 shows TBRF ImmunoBlots of representative patient serum samples. Positive immunoblots were further characterized for the presence of antibodies to one or more RFB species, and instances of infection with more than one RFB species were identified (Table 2). Immunoblot testing of control sera demonstrated excellent specificity of 97.1% for the TBRF assay (Table 2). As shown in FIG. 3, various combinations of SEQ ID NOs: 1-11 were identified in patient serum samples, demonstrating that antigens from multiple species are required for an inclusive test.

These results illustrated how detection of antibodies to TBRF *Borrelia* species identified patients with Chronic Lyme Disease symptoms that would otherwise be missed by only testing for *Borrelia burgdorferi* antigens. These results also confirmed that the serotype makeup of TBRF *Borrelia* exposure is complex, thereby showing the power and importance of inclusivity in TBRF testing, that is, simultaneous testing for antigens from multiple TBRF species.

TABLE 1

| | Reference human sera for determining specificity of *B. Burgdorferi* species and RFB species immunoblots | | | |
|---|---|---|---|---|
| Source | Characteristic | Total No. of Sera | BbsI Immunoblots (+) | RFB Immunoblots (+) |
| CDC Reference | Fibromyalgia | 2 | 0 | 0 |
| Set (n = 25) | Healthy endemic | 7 | 1 | 0 |
| | Healthy non-endemic | 6 | 0 | 0 |
| | Mononucleosis | 2 | 0 | 0 |
| | Multiple sclerosis | 2 | 0 | 1 |
| | Rheumatoid arthritis | 2 | 0 | 0 |
| | Severe Periodontitis | 2 | 0 | 0 |
| | Syphilis | 2 | 0 | 1 |
| | Autoimmune | | | |
| CAP and NYSHD | ANA (+) | 3 | 0 | 0 |
| (n = 42) | ANA (−) | 2 | 0 | 0 |
| Autoimmunity | DNA (+) | 1 | 0 | 0 |
| and Allergy | Rheumatoid factor (+) | 9 | 0 | 0 |
| | Rheumatoid factor (−) | 8 | 0 | 0 |
| | Allergy (n = 19) | | | |
| | IgG (+) | 13 | 0 | 1 |
| | Spec. IgE (+) | 4 | 0 | 0 |
| | Spec. IgE (−) | 2 | 0 | 0 |
| NYB (n = 21) | Epstein-Barr virus (EBV) | 4 | 1 | 0 |
| Viruses and | Human immunodeficiency | 4 | 0 | 0 |
| RPR (+) | virus (HIV) | | | |
| | Cytomegalovirus (CMV) | 5 | 0 | 1 |
| | Hepatitis C virus (HCV) | 0 | 0 | 0 |
| | RPR (+) | 8 | 2 | 1 |
| IGeneX (n = 87) | *Bartonella henselae* infection | 7 | 0 | 0 |
| | Human granulocytic anaplasmosis | 16 | 0 | 0 |
| | *Babesia microti* infection | 14 | 0 | 0 |
| | *Babesia duncani* Infection | 41 | 0 | 0 |
| | Human monocytic ehrlichiosis | 5 | 0 | 0 |
| | Negative controls | 4 | 0 | 0 |
| | False Positives | 175 | 4 | 5 |
| | Specificity | | 97.7% | 97.1% |

ANA—anti-nuclear antibodies; CAP—College of American Pathologists; CDC—Center for Disease Control; NYB—New York Biologics, Southampton, NY; NYSH—New York State Department of Health; RF—rheumatoid factor; RPR—rapid plasma regain test for syphilis.

TABLE 2

| Summary of seroreactivity for subjects in Group 1 (*B. Burgdorferi* species), Group 2 (RFB species), or both | |
| --- | --- |
| Immuno Blot | Total |
| Group 1 BbsI Positive | 42 |
| Group 2 RFB Positive | 56 |
| Dual Group 1 and 2 Positive | 8 |
| Group 2. RFB Positive Samples | 48 (53%) |
| RFB alone | 25 |
| *B. hermsii* alone | 7 |
| *B. miyamotoi* alone | 4 |
| *B. turicatae* alone | 8 |
| *B. turcica* alone | 2 |
| *B. hermsii* + *B. turcica* | 1 |
| *B. hermsii* + *B. miyamotoi* | 1 |
| Dual Group 1 and 2 | 8 (9%) |
| Bb + RFB | 2 |
| Bb + *B. hermsii* | 1 |
| *B. californiensis* + RFB | 2 |
| *B. spielmanii* + RFB | 1 |
| *B. afzelii/garinii* + RFB | 1 |
| *B. afzelii/garinii* + *B. turicatae* | 1 |
| Total cases | 56 |

Discussion for Examples 1-2

TBRF are found worldwide and are a significant cause of morbidity and mortality, particularly with respect to unexplained fever cases. Advances in molecular testing have led to widespread identification of *Borrelia* species in human specimens, thus challenging prevailing thought regarding geographic distribution and prevalence of RFB infection. Although RFB is a growing concern in the Western United States, Central America, and South America, TBRF is not reportable nationally in the United States, and there is no standard case definition. In 2011, TBRF was reportable in 12 Western states, yielding 504 cases, with 70% of the cases reported in three states: California (33%), Washington (25%), and Colorado (11%). Disease-causing species in the United States include *B. miyamotoi, B. hermsii, B. lonestari, B. parkeri, B. turicatae*, and *B. mazzotii*. Most cases in the USA are caused by *B. hermsii*, transmitted by *Ornithodoros hermsi* ticks, but *B. miyamotoi, B. hermsii*, and *B. parkeri* human infections were reported in California, and *B. coriaceae* was detected in ticks, although human infection was not confirmed [Fesler et al. Healthcare 8(2): 97-112 (2020)].

The genetic diversity of *Borrelia* spirochetes, as well as the symptoms of infection that are as diverse as the organisms causing them, makes it challenging to diagnose *Borrelia*-associated disease. In summary, exposure to TBRF *Borrelia* is a cause for concern, and TBRF *Borrelia* may explain Lyme Disease symptoms in patients who are seronegative for *B. burgodorferi* sensu lato species. As shown herein, some patients may demonstrate dual exposure to both *B. burgodorferi* and TBRF species, further complicating diagnosis and treatment. Immunoblot testing for RFB species using methods and compositions of the invention allows the detection of a diverse group of TBRF *Borrelia* serotypes and provides a greater understanding of human exposure to pathogenic *Borrelia*.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A composition comprising one or more labeled and/or bound amino acid sequences selected from the group consisting of:

SEQ ID NO: 1;
SEQ ID NO: 2;
SEQ ID NO: 3;
SEQ ID NO: 4;
SEQ ID NO: 5 and variants thereof having at least 90% homology;
SEQ ID NO: 6 and variants thereof having at least 90% homology;
SEQ ID NO: 7;
SEQ ID NO: 8;
SEQ ID NO: 9;
SEQ ID NO: 10; and
SEQ ID NO: 11 and variants thereof having at least 96% homology;

wherein, when labeled, the one or more amino acid sequences are labeled with biotin/streptavidin, enzyme conjugates, fluorescent moieties, or biological fluorophores, wherein, when bound, the one or more amino acid sequences are bound to a substance selected from the group consisting of nitrocellulose, nylon, polyvinylidene difluoride (PVDF), magnetic beads, and agarose.

2. A method for detecting antibodies resulting from infection by one or more members of Tick-Borne Relapsing Fever (TBRF) *Borrelia* genus if present in a biological sample from a subject suspected of having TBRF, the method comprising:

providing the biological sample obtained from the subject suspected of having TBRF;

contacting the biological sample with a composition comprising one or more labeled and/or bound amino acid sequences selected from the group consisting of:

SEQ ID NO: 1;
SEQ ID NO: 2;
SEQ ID NO: 3:
SEQ ID NO: 4;
SEQ ID NO: 5 and variants thereof having at least 90% homology;
SEQ ID NO: 6 and variants thereof having at least 90% homology;
SEQ ID NO: 7;
SEQ ID NO: 8;
SEQ ID NO: 9;
SEQ ID NO: 10; and
SEQ ID NO: 11 and variants thereof having at least 96% homology;

wherein, when labeled, the one or more amino acid sequences are labeled with biotin/streptavidin, enzyme conjugates, fluorescent moieties, or biological fluorophores, wherein, when bound, the one or more amino acid sequences are bound to a substance selected from the group consisting of nitrocellulose, nylon, polyvinylidene difluoride (PVDF), magnetic beads, and agarose; and detecting a positive immunobinding reaction which indicates the presence of one or more TBRF specific antibodies in the biological sample.

3. The method of claim 2, wherein the biological sample is considered positive for TBRF if at least two positive immunobinding reactions are detected.

4. The method of claim 2, wherein the positive immuno-binding reaction is detected with anti-human IgG or anti-human IgM antibody linked to a detectable moiety.

5. The method of claim 4, wherein the detectable moiety is selected from the group consisting of chromophores, radioactive moieties and enzymes.

6. The method of claim 4, wherein the detectable moiety comprises alkaline phosphatase.

7. The method of claim 4, wherein the detectable moiety comprises biotin.

8. The composition of claim 1, wherein the variants of SEQ ID NOs: 5 and 6 have at least 95% homology.

9. The composition of claim 8, wherein the one or more labeled and/or bound amino acid sequences are selected from the group consisting of SEQ ID NOs: 1-11.

*  *  *  *  *

SEQUENCE LISTING

<160> NUMBER OF SEQ ID NOS: 11

<210> SEQ ID NO 1
<211> LENGTH: 342
<212> TYPE: PRT
<213> ORGANISM: Borrelia hermsii

<400> SEQUENCE: 1

-continued

```
Met Gln Gln Pro Glu Ala Gly Lys Thr Gly Val Ser Gly Gly Val Asn
1               5                   10                  15

Gly Asn Leu Gly Asn Ser Leu Met Glu Leu Gly Arg Ser Ala Glu Asn
            20                  25                  30

Ala Phe Tyr Ala Phe Ile Glu Leu Val Ser Asp Val Leu Gly Phe Thr
            35                  40                  45

Ala Lys Ser Asp Thr Thr Lys Gln Glu Val Gly Gly Tyr Phe Asn Ser
    50                  55                  60

Leu Gly Ala Lys Leu Gly Glu Ala Ser Asn Asp Leu Glu Gln Val Ala
65                  70                  75                  80

Val Lys Ala Glu Thr Gly Val Asp Lys Ser Asp Ser Ser Lys Asn Pro
                85                  90                  95

Ile Arg Glu Ala Val Asn Glu Ala Lys Glu Val Leu Gly Thr Leu Lys
            100                 105                 110

Gly Tyr Val Glu Ser Leu Gly Thr Ile Gly Asp Ser Asn Pro Val Gly
            115                 120                 125

Tyr Ala Asn Asn Ala Ala Gly Ser Gly Thr Thr Ala Ala Asp Asp Glu
            130                 135                 140

Leu Arg Lys Ala Phe Lys Ala Leu Gln Glu Ile Val Lys Ala Ala Thr
145                 150                 155                 160

Asp Ala Gly Val Lys Ala Leu Lys Ile Gly Ala Thr Thr Leu Gln Ala
                165                 170                 175

Asn Gly Gly Ala Asp Asn Lys Glu Gly Ala Lys Ile Leu Ala Thr Ser
            180                 185                 190

Gly Gly Asn Pro Ala Ala Ala Asp Val Ala Lys Ala Ala Ala Ile Leu
            195                 200                 205

Ser Ser Val Ser Gly Glu Glu Met Leu Ser Ser Ile Val Lys Ser Gly
    210                 215                 220

Glu Asn Asp Ala Gln Leu Ala Ala Ala Ala Asp Gly Asn Thr Ser Ala
225                 230                 235                 240

Ile Ser Phe Ala Lys Gly Gly Ser Asp Ala His Leu Ala Gly Ala Asn
                245                 250                 255

Thr Pro Lys Ala Ala Ala Val Ala Gly Gly Ile Ala Leu Arg Ser Leu
            260                 265                 270

Val Lys Thr Gly Lys Leu Ala Ala Gly Ala Ala Asp Asn Ala Thr Gly
            275                 280                 285

Gly Gly Lys Glu Val Gln Gly Val Gly Val Ala Ala Ala Asn Lys Leu
            290                 295                 300

Leu Arg Ala Val Glu Asp Val Ile Lys Lys Thr Val Lys Asn Val Leu
305                 310                 315                 320

Glu Lys Ala Lys Glu Lys Ile Asp Lys Ala Arg Gly Ser Gln Glu Pro
                325                 330                 335

Val Ser Glu Ser Ser Lys
            340
```

<210> SEQ ID NO 2
<211> LENGTH: 283
<212> TYPE: PRT
<213> ORGANISM: Borrelia turicatae

<400> SEQUENCE: 2

```
Met Asp Asn Val Met Ser Gly Ile Asp Asn Val Ile Gln Gly Ala Gly
1               5                   10                  15

Thr Phe Ala Thr Ala Ala Met Gln Gly Val Gly Thr Val Ile Asp Val
            20                  25                  30
```

Leu Gln Asp Val Gly Thr Phe Val Ile Ser Asp Ile Gln Asn Met Gly
        35                  40                  45

Ala Arg Met Leu Phe Gly Thr Gly Glu Asn Ser Ser Val Ala Ser Glu
        50                  55                  60

Gly Ser Glu Ser Val Met Ser Leu Ser Ser Asn Asp Ser Ser Glu Ala
65                  70                  75                  80

Lys Asp Val Thr Val Val Leu Ser Ser Asp Val Thr Ser Lys Gly Asn
                85                  90                  95

Asp Val Ala Val Gly Leu Ser Ser Asp Glu Thr Gln Val Ile Gly Arg
                100                 105                 110

Leu Glu Lys Tyr Leu Gln Ser Ala Ile Lys Ile Asn Gly Arg Ser Asp
        115                 120                 125

Ser Asp Gln Ser Asn Leu Glu Ser Gly Arg Lys Lys Phe Phe Asn Trp
        130                 135                 140

Leu Lys Thr Ser Asp Thr Asn Ala Ser Lys Arg Lys Glu Leu Val Gln
145                 150                 155                 160

Asp Leu Gln Lys Val Phe Asp Leu Ile Lys Glu Lys Ser Ser Asp Ser
                165                 170                 175

Thr Glu Leu Lys His Trp Val Gln Ser Ile Val Asp Arg Ile Glu Asp
        180                 185                 190

Lys Ser Thr Ile Val Asp Ile Asp Ser Asp Asp Glu Leu Asn Asn Asp
        195                 200                 205

Lys Glu Val Asp Phe Leu Ile Glu Asn Thr Leu Ala Ser Arg Asp Tyr
        210                 215                 220

Ser Gly Phe Ala Val Ser Leu Leu Phe Gln Ser Leu Ala Asp Thr Leu
225                 230                 235                 240

Tyr Asp Ser Asp Asn Asn Arg Asp Lys Ser Glu Glu Gln Ile Phe Gln
                245                 250                 255

Asp Leu Arg Lys Val Phe Ser Asp Ser Ser Asp Lys Ser Glu Gly Val
                260                 265                 270

Leu Gly Phe Lys Ser Lys Ile Glu Ala Thr Asn
        275                 280

```
<210> SEQ ID NO 3
<211> LENGTH: 165
<212> TYPE: PRT
<213> ORGANISM: Borrelia turicatae

<400> SEQUENCE: 3
```

Met Ser Glu Thr Ser Leu Leu Asn Ile Glu Thr Asn Leu Leu Asn Thr
1                   5                   10                  15

Leu Asp Asp Asn Gln Lys Gln Ala Leu Ile Thr Phe Lys Asp Leu Leu
                20                  25                  30

Gln Asp Lys Lys His Leu Ser Ile Leu Glu Lys Gln Gln Lys Ser Ile
        35                  40                  45

Leu Glu Asp Leu Lys Ala Asn Gln Lys Asn Tyr Asn Leu Gln Asp Lys
        50                  55                  60

Leu Lys Lys Thr Leu Asn Ser Glu Tyr Asp Lys Asn Gln Leu Asn Lys
65                  70                  75                  80

Leu Phe Asp Glu Leu Gly Asn Ile Lys Thr Lys Gln Phe Leu Gln Gln
                85                  90                  95

Leu His Ile Ile Leu Gln Ser Ile Lys Asp Gly Lys Pro Thr Asn Phe
        100                 105                 110

Ala Ser Ser Asn Phe Asn Asn Leu Asn Gln Thr Leu Glu Gln Lys Lys

```
                115                 120                 125

Glu Gln Ala Leu Lys Tyr Ile Lys Asp Lys Leu Tyr Thr Asp Tyr Tyr
    130                 135                 140

Leu Tyr Ile Asn Gly Ile Gln Asp Ala Asn Tyr Phe Phe Glu Arg Ile
145                 150                 155                 160

Met Ser Leu Leu Glu
                165

<210> SEQ ID NO 4
<211> LENGTH: 322
<212> TYPE: PRT
<213> ORGANISM: Borrelia turicatae

<400> SEQUENCE: 4

Met Arg Asn Asn Ser Ile Asn Ala Ala Asn Leu Ser Lys Thr Gln Glu
1                   5                   10                  15

Lys Leu Ser Ser Gly His Arg Ile Asn Arg Ala Ser Asp Asp Ala Ala
                20                  25                  30

Gly Met Gly Val Ala Gly Lys Ile Asn Ala Gln Ile Arg Gly Leu Ser
                35                  40                  45

Gln Ala Ser Arg Asn Thr Ser Lys Ala Ile Asn Phe Ile Gln Thr Thr
    50                  55                  60

Glu Gly Asn Leu Asn Glu Val Glu Lys Val Leu Val Arg Met Lys Glu
65                  70                  75                  80

Leu Ala Val Gln Ser Gly Asn Gly Thr Tyr Ser Asp Ala Asp Arg Gly
                85                  90                  95

Ser Ile Gln Ile Glu Ile Glu Gln Leu Thr Asp Glu Ile Asn Arg Ile
                100                 105                 110

Ala Asp Gln Ala Gln Tyr Asn Gln Met His Met Leu Ser Asn Lys Ser
                115                 120                 125

Ala Ala Gln Asn Ile Lys Thr Ala Glu Glu Leu Gly Met Gln Pro Ala
    130                 135                 140

Lys Ile Asn Thr Pro Ala Ser Leu Ala Gly Ser Gln Ala Ser Trp Thr
145                 150                 155                 160

Leu Arg Val His Val Gly Ala Asn Gln Asp Glu Ala Ile Ala Val Asn
                165                 170                 175

Ile Tyr Ala Ala Asn Val Ala Asn Leu Phe Ala Gly Glu Gly Ala Gln
                180                 185                 190

Val Ser Pro Ala Gln Glu Gly Ala Gln Gln Glu Gly Val Gln Ala Ala
                195                 200                 205

Pro Ala Pro Ala Ala Ala Pro Ala Gln Gly Gly Val Asn Ser Pro Val
    210                 215                 220

Asn Val Thr Thr Thr Ile Asp Ala Asn Met Ser Leu Ser Lys Ile Glu
225                 230                 235                 240

Asn Ala Ile Arg Met Val Ser Asp Gln Arg Ala Asn Leu Gly Ala Phe
                245                 250                 255

Gln Asn Arg Leu Glu Ser Ile Lys Ala Ser Thr Glu Tyr Ala Ile Glu
                260                 265                 270

Asn Leu Lys Ser Ser Tyr Ala Gln Ile Gln Asp Ala Thr Met Thr Asp
                275                 280                 285

Glu Ile Val Ala Ser Thr Thr Asn Ser Ile Leu Thr Gln Ser Ala Met
    290                 295                 300

Ala Met Ile Ala Gln Ala Asn Gln Val Pro Gln Tyr Val Leu Ser Leu
305                 310                 315                 320
```

-continued

Leu Arg

<210> SEQ ID NO 5
<211> LENGTH: 252
<212> TYPE: PRT
<213> ORGANISM: Borrelia parkeri

<400> SEQUENCE: 5

Met Asp Met Gly Ser Thr Arg Asp Trp Leu Thr Asn Asp Asp Gly Phe
1               5                   10                  15

Val Arg Gly Thr Lys Gly Phe Asp Asp Ser Pro Phe Arg Arg Pro Asp
                20                  25                  30

Arg Val Asp Lys Glu Val Ser Ala Gly Gly Arg Glu Ile Glu Lys Ala
            35                  40                  45

Phe Ser Arg Asn Leu Gly Val Ala Gly Gly Gln Arg Lys Gly Thr Asp
        50                  55                  60

Asp Val Lys Asn Gly Ile Ala Gly Ala Arg Glu Ser Gly Gly Val Leu
65                  70                  75                  80

Lys Glu Ala Glu Asn Ala Gly Gln Arg Asp Val Asp Asp Ser Gly Glu
                85                  90                  95

Gly Ile Lys Asn Asp Val Ile Gln Asn Leu Gly Ser Val Gly Val Gln
            100                 105                 110

Val Ala Val Gly Ser Glu Asn Asn Gly Asp Asp Ser Gly Gln Glu Ala
            115                 120                 125

Glu Lys Gly Ser Gln Asn Leu Gly Asp Thr Gly Thr Gln Arg Val Val
        130                 135                 140

Ser Thr Ser Asp Leu Asn Ser His Leu Gly Val Glu Ser Lys Gly Gly
145                 150                 155                 160

Met Ser Thr Asn Lys Glu Gly Ile Ser Thr Asn His Val Thr Glu Asn
                165                 170                 175

Arg Asn Ser Ile Asn Ser Ile Thr Ser Thr Ser Gly Leu Ser Thr
                180                 185                 190

Ala Leu Gln Ile Ala Gly Thr Ser Thr Arg Ala Ser Gly Tyr Glu Gly
        195                 200                 205

Glu Val Thr Thr Asn Ala Gln Asp Arg Ser Phe Ile Asp Thr Lys Thr
        210                 215                 220

Gln Asp Ser Lys Lys Gln Tyr Ser Asp Phe Ser Asp Gln Asp Ile Arg
225                 230                 235                 240

Asp Lys Ile Leu Gly Asn Val Val Gly Gly Val Val
                245                 250

<210> SEQ ID NO 6
<211> LENGTH: 280
<212> TYPE: PRT
<213> ORGANISM: Borrelia parkeri

<400> SEQUENCE: 6

Met Gly Asn Val Met Ser Gly Ile Asp Asn Val Ile Gln Gly Ala Gly
1               5                   10                  15

Thr Phe Ala Thr Ala Ala Met Gln Gly Val Gly Thr Val Ile Asp Val
                20                  25                  30

Leu Gln Asp Val Gly Thr Phe Val Ile Ser Asp Ile Gln Asn Met Gly
            35                  40                  45

Ala Arg Met Phe Phe Gly Thr Gly Glu Ser Ser Ser Val Ala Ser Glu
        50                  55                  60

Asp Ser Glu Ser Val Met Ser Leu Ser Ser Lys Ala Ser Ser Glu Ala

-continued

```
65              70              75              80

Lys Asp Thr Thr Val Gly Leu Ser Ser Asp Val Thr Ser Lys Gly Asn
                85              90              95

Asn Val Ala Val Gly Leu Ser Ser Asp Glu Ile Gln Ile Ile Gly Arg
                100             105             110

Leu Glu Lys Tyr Leu Lys Ser Ala Ile Lys Ile Asn Gly Arg Ser Asp
            115             120             125

Ser Asp Gln Ser Lys Leu Glu Ser Gly His Lys Lys Phe Phe Gln Trp
    130             135             140

Leu Lys Thr Ser Asp Thr Asn Ala Ser Lys Arg Lys Glu Leu Val Gln
145             150             155             160

Asn Leu Gln Arg Val Phe Asn Leu Ile Lys Glu Lys Ser Ser Asp Ser
                165             170             175

Thr Glu Leu Lys Lys Trp Met Gln Ser Ile Val Asp Asp Ile Glu Asn
            180             185             190

Lys Ser Thr Ile Ile Asp Ile Asn Ser Asp Asp Lys Leu Asn Asn Asp
            195             200             205

Lys Glu Val Asp Phe Leu Ile Glu Lys Thr Leu Gly Ser Ser Asp Tyr
    210             215             220

Ser Gly Phe Ala Val Ser Leu Leu Phe Gln Ala Leu Ala Asp Thr Leu
225             230             235             240

Tyr Asp Ser Glu Asn Ser Arg Asp Lys Ser Glu Glu Gln Ile Phe Lys
                245             250             255

Asp Leu Arg Lys Val Phe Ser Asp Lys Ser Glu Gly Val Leu Glu Phe
                260             265             270

Lys Ser Lys Ile Glu Ala Thr Asn
            275             280

<210> SEQ ID NO 7
<211> LENGTH: 319
<212> TYPE: PRT
<213> ORGANISM: Borrelia parkeri

<400> SEQUENCE: 7

Met Cys Gln Asn Glu Lys Met Ser Met Thr Asn Lys Lys Ser Pro Leu
1               5               10              15

Thr Ile Ala His Arg Gly Ala Ser Gly Tyr Leu Pro Glu His Thr Leu
                20              25              30

Glu Ser Lys Ala Phe Ala Tyr Ala Leu Gly Ala Asp Tyr Leu Glu Gln
            35              40              45

Asp Ile Val Leu Thr Lys Asp Asn Val Pro Ile Ile Met His Asp Pro
    50              55              60

Glu Leu Asp Thr Thr Thr Asn Val Ala Lys Leu Phe Pro Glu Arg Ala
65              70              75              80

Arg Glu Asn Gly Arg Tyr Tyr Ser Val Asp Phe Thr Leu Asp Glu Leu
                85              90              95

Lys Ser Leu Ser Leu Ser Glu Arg Phe Asp Leu Glu Thr Arg Lys Pro
                100             105             110

Ile Tyr Pro Lys Arg Phe Pro Leu Asn Glu Tyr Asn Phe Lys Ile Pro
            115             120             125

Thr Leu Glu Glu Glu Ile Gln Phe Ile Gln Gly Leu Asn Lys Ser Thr
            130             135             140

Gly Arg Asn Val Gly Ile Tyr Pro Glu Ile Lys Lys Pro Leu Trp His
145             150             155             160
```

-continued

```
Lys Gln Gln Gly Lys Asp Ile Ser Lys Ile Val Ile Glu Ile Leu Asn
            165             170             175

Lys Tyr Gly Tyr Lys Ser Lys Glu Asp Lys Ile Tyr Leu Gln Thr Phe
            180             185             190

Asp Phe Asp Glu Leu Lys Arg Ile Arg Glu Glu Leu Gly Tyr Gln Gly
            195             200             205

Lys Leu Ile Met Leu Val Gly Glu Asn Asp Trp Asn Glu Ala Pro Thr
    210             215             220

Asp Tyr Glu Tyr Ile Lys Ser Gln Glu Gly Met Thr Glu Val Ala Lys
225             230             235             240

Tyr Ala Asp Gly Ile Gly Pro Trp Ile Pro Gln Ile Ile Ile Asp Gly
            245             250             255

Lys Ile Thr Asp Leu Thr Ser Leu Ala His Lys Tyr Asn Met Glu Val
            260             265             270

His Ala Tyr Thr Phe Arg Ile Asp Ser Leu Pro Ser Tyr Val Lys Asp
            275             280             285

Ala Asn Glu Leu Leu Asp Leu Leu Phe Asn Gln Ala Lys Ile Asp Gly
    290             295             300

Leu Phe Thr Asp Phe Thr Asp Thr Val Val Lys Phe Ile Lys Gln
305             310             315

<210> SEQ ID NO 8
<211> LENGTH: 159
<212> TYPE: PRT
<213> ORGANISM: Borrelia parkeri

<400> SEQUENCE: 8

Met Ser Glu Thr Ser Leu Leu Asn Thr Leu Asp Asn Asn Gln Lys Gln
1               5               10              15

Ala Leu Ile Thr Phe Lys Asp Leu Leu Gln Asp Lys Asn His Arg Ser
            20              25              30

Ile Leu Glu Lys Gln Gln Lys Ser Ile Leu Lys Asp Leu Glu Lys His
            35              40              45

Gln Glu Asn Ser Asn Leu Gln Asp Lys Leu Lys Lys Thr Leu Asn Ser
    50              55              60

Glu Tyr Asp Lys Thr Gln Leu Asn Lys Leu Phe Asp Glu Leu Gly Asn
65              70              75              80

Ile Lys Thr Lys Gln Phe Leu Gln Lys Leu His Ile Met Leu Lys Ser
            85              90              95

Ile Asn Asn Gly Thr Leu Thr Ser Phe Ser Ser Ser Asn Phe Lys Asp
            100             105             110

Ser Asn Gln Thr Leu Glu Gln Lys Lys Glu Gln Ala Leu Gln Tyr Ile
            115             120             125

Lys Gly Gln Leu Tyr Thr Asp Tyr Tyr Leu Tyr Ile Asn Gly Ile Gln
            130             135             140

Asp Ala Asn Tyr Phe Phe Glu Arg Ile Met Ser Val Leu Glu Ile
145             150             155

<210> SEQ ID NO 9
<211> LENGTH: 322
<212> TYPE: PRT
<213> ORGANISM: Borrelia parkeri

<400> SEQUENCE: 9

Met Arg Asn Asn Ser Ile Asn Ala Ala Asn Leu Arg Lys Thr Gln Glu
1               5               10              15
```

-continued

```
Lys Leu Ser Ser Gly His Arg Ile Asn Arg Ala Ser Asp Asp Ala Ala
            20              25              30

Gly Met Gly Val Ala Gly Lys Ile Asn Ala Gln Ile Arg Gly Leu Ser
            35              40              45

Gln Ala Ser Arg Asn Thr Ser Lys Ala Ile Asn Phe Ile Gln Thr Thr
        50              55              60

Glu Gly Asn Leu Asn Glu Val Glu Lys Val Leu Val Arg Met Lys Glu
65              70              75              80

Leu Ala Val Gln Ser Gly Asn Gly Thr Tyr Ser Asp Ala Asp Arg Gly
                85              90              95

Ser Ile Gln Ile Glu Ile Glu Gln Leu Thr Asp Glu Ile Asn Arg Ile
            100             105             110

Ala Asp Gln Ala Gln Tyr Asn Gln Met His Met Leu Ser Asn Lys Ser
            115             120             125

Ala Ala Gln Asn Ile Lys Thr Ala Glu Glu Leu Gly Met Gln Pro Ala
        130             135             140

Lys Ile Asn Thr Pro Ala Ser Leu Ala Gly Ala Gln Ala Ser Trp Thr
145             150             155             160

Leu Arg Val His Val Gly Ala Asn Gln Asp Glu Ala Ile Ala Val Asn
                165             170             175

Ile Tyr Ala Ser Asn Val Ala Asn Leu Phe Ala Gly Glu Gly Ala Gln
            180             185             190

Val Ser Pro Ala Gln Glu Gly Ala Gln Gln Glu Gly Val Gln Ala Ala
            195             200             205

Pro Ala Pro Ala Ala Ala Pro Ala Gln Gly Gly Val Asn Ser Pro Val
        210             215             220

Asn Val Thr Thr Thr Val Asp Ala Asn Met Ser Leu Ser Lys Ile Glu
225             230             235             240

Asn Ala Ile Arg Met Val Ser Asp Gln Arg Ala Asn Leu Gly Ala Phe
                245             250             255

Gln Asn Arg Leu Glu Ser Ile Lys Ala Ser Thr Glu Tyr Ala Ile Glu
            260             265             270

Asn Leu Lys Ser Ser Tyr Ala Gln Ile Lys Asp Ala Thr Met Thr Asp
            275             280             285

Glu Ile Val Ala Ser Thr Thr Asn Ser Ile Leu Thr Gln Ser Ala Met
        290             295             300

Ala Met Ile Ala Gln Ala Asn Gln Val Pro Gln Tyr Val Leu Ser Leu
305             310             315             320

Leu Arg

<210> SEQ ID NO 10
<211> LENGTH: 314
<212> TYPE: PRT
<213> ORGANISM: Borrelia duttonii

<400> SEQUENCE: 10

Met Glu Asn Ala Lys Ile Asn Lys Lys Ser Ala Leu Ile Ile Ala His
1               5               10              15

Arg Gly Ala Ser Gly Tyr Leu Pro Glu His Thr Leu Glu Ala Lys Ala
            20              25              30

Tyr Ala His Ala Leu Gly Ala Asp Tyr Ile Glu Gln Asp Ile Val Leu
            35              40              45

Thr Lys Asp Asp Ile Pro Ile Val Met His Asp Pro Glu Leu Asp Thr
        50              55              60
```

-continued

```
Thr Thr Asn Val Ala Lys Leu Phe Pro Gly Arg Ala Arg Glu Asn Gly
65                  70                  75                  80

Lys Tyr Tyr Ser Val Asp Phe Thr Leu Ala Glu Ile Lys Ser Leu Ser
                85                  90                  95

Leu Ser Glu Arg Phe Asp Pro Glu Thr Gln Gln Pro Ile Tyr Pro Asn
            100                 105                 110

Arg Phe Pro Ala Thr Glu Tyr Asp Phe Lys Ile Pro Thr Leu Glu Glu
        115                 120                 125

Glu Ile Lys Phe Ile Gln Gly Leu Asn Lys Ser Thr Gly Lys Asn Ile
    130                 135                 140

Gly Ile Tyr Pro Glu Ile Lys Lys Pro Leu Trp His Lys Gln Gln Gly
145                 150                 155                 160

Lys Asp Ile Ser Lys Ile Val Ile Asp Ile Leu Asn Lys Tyr Gly Tyr
                165                 170                 175

Lys Ser Lys Glu Asp Lys Ile Tyr Leu Gln Thr Phe Asp Phe Asp Glu
            180                 185                 190

Ile Lys Arg Ile Arg Glu Glu Leu Gly Tyr Gln Gly Lys Leu Ile Met
        195                 200                 205

Leu Val Gly Glu Asn Asp Trp Glu Glu Ala Pro Thr Asp Tyr Glu Tyr
    210                 215                 220

Ile Lys Ser Glu Glu Gly Met Ala Glu Val Ala Lys Tyr Ala Asp Gly
225                 230                 235                 240

Ile Gly Pro Trp Ile Pro Gln Ile Ile Ile Asn Gly Gln Ile Thr Gly
                245                 250                 255

Leu Ile Ser Leu Ala His Lys Tyr Asn Met Gln Val His Pro Tyr Thr
            260                 265                 270

Phe Arg Ile Asp Ala Leu Pro Ser Tyr Val Lys Asp Pro Asn Glu Leu
        275                 280                 285

Leu Glu Leu Leu Phe Ile Lys Ala Lys Val Asp Gly Leu Phe Thr Asp
    290                 295                 300

Phe Val Asp Ile Ser Ile Lys Phe Met Gln
305                 310
```

```
<210> SEQ ID NO 11
<211> LENGTH: 327
<212> TYPE: PRT
<213> ORGANISM: Borrelia miyamotoi

<400> SEQUENCE: 11
```

```
Met Ala Ser Met Thr Gly Gly Gln Gln Met Gly Arg Gly Ser Glu Met
1               5                   10                  15

Gly Glu Asn Lys Lys Ser Pro Leu Ile Ile Ala His Arg Gly Ala Ser
                20                  25                  30

Gly Tyr Leu Pro Glu His Thr Leu Glu Ala Lys Ala Tyr Ala Tyr Ala
            35                  40                  45

Leu Gly Ala Asp Tyr Leu Glu Gln Asp Ile Val Leu Thr Lys Asp Asn
        50                  55                  60

Ile Pro Val Ile Met His Asp Pro Glu Ile Asp Thr Thr Thr Asn Val
65                  70                  75                  80

Ala Gln Leu Phe Pro Asn Arg Ala Arg Glu Asn Gly Arg Tyr Tyr Ala
                85                  90                  95

Thr Asp Phe Thr Leu Thr Glu Leu Lys Ser Leu Asn Leu Ser Glu Arg
            100                 105                 110

Phe Asp Pro Glu Asn Lys Lys Pro Ile Tyr Pro Asn Arg Phe Pro Leu
        115                 120                 125
```

-continued

```
Asn Glu Tyr Asn Phe Lys Ile Pro Thr Leu Glu Glu Glu Ile Gln Phe
    130             135                 140

Ile Gln Gly Leu Asn Lys Ser Thr Gly Lys Asn Val Gly Ile Tyr Pro
145             150                 155                 160

Glu Ile Lys Lys Pro Phe Trp His Lys Gln Gln Gly Lys Asp Ile Ser
            165                 170                 175

Lys Ile Val Ile Glu Ile Leu Asn Lys Tyr Gly Tyr Lys Ser Lys Glu
            180                 185                 190

Asp Lys Ile Tyr Leu Gln Thr Phe Asp Phe Asp Glu Leu Lys Arg Ile
        195                 200                 205

Arg Lys Glu Leu Gly Tyr Gln Gly Lys Leu Ile Met Leu Val Gly Glu
    210                 215                 220

Asn Asp Trp Asn Glu Ala Pro Thr Asp Tyr Glu Tyr Ile Lys Ser Glu
225                 230                 235                 240

Glu Gly Ile Ala Glu Val Ala Lys Tyr Ser Asp Gly Ile Gly Pro Trp
            245                 250                 255

Ile Pro Gln Ile Ile Ile Asp Gly Lys Ile Thr Glu Leu Thr Asn Leu
            260                 265                 270

Ala His Lys Tyr Asn Ile Glu Val His Pro Tyr Thr Phe Arg Thr Asp
        275                 280                 285

Ala Leu Pro Ser Tyr Val Lys Asn Glu Asn Glu Leu Leu Asp Leu Leu
    290                 295                 300

Phe Asn Lys Ala Lys Val Asp Gly Ile Phe Thr Asp Phe Thr Asp Thr
305                 310                 315                 320

Val Met Asn Phe Ile Lys Lys
                325
```